United States Patent
Chang et al.

(10) Patent No.: US 9,343,776 B2
(45) Date of Patent: May 17, 2016

(54) ELECTROLYTE FOR ELECTROCHEMICAL DEVICE AND THE ELECTROCHEMICAL DEVICE THEREOF

(75) Inventors: Chia-Chin Chang, Kaohsiung County (TW); Li-Jane Her, Kaohsiung County (TW)

(73) Assignee: Taiwan Hopax Chems. Mfg Co., Ltd. (TW)

( * ) Notice: Subject to any disclaimer, the term of this patent is extended or adjusted under 35 U.S.C. 154(b) by 974 days.

(21) Appl. No.: 13/352,498

(22) Filed: Jan. 18, 2012

(65) Prior Publication Data

US 2012/0196158 A1 Aug. 2, 2012

(30) Foreign Application Priority Data

Feb. 1, 2011 (TW) .............................. 100103839 A

(51) Int. Cl.
*H01M 10/056* (2010.01)
*H01M 10/0567* (2010.01)
(Continued)

(52) U.S. Cl.
CPC ............. *H01M 10/0567* (2013.01); *C07F 5/02* (2013.01); *C07F 5/025* (2013.01); *H01M 10/0525* (2013.01); *Y02E 60/122* (2013.01)

(58) Field of Classification Search
CPC .................... H01M 10/0567; H01M 10/0525; C07F 5/02; C07F 5/025; Y02E 60/122
USPC .................................... 429/50, 336, 339, 341
See application file for complete search history.

(56) References Cited

U.S. PATENT DOCUMENTS

| 6,352,798 B1 | 3/2002 | Lee et al. | |
| 2003/0073006 A1* | 4/2003 | Fujinami et al. | 429/336 |

(Continued)

FOREIGN PATENT DOCUMENTS

JP 2010251313 A * 11/2010

OTHER PUBLICATIONS

Watari; Machine translation of JP 2010251313 A, Japan, Nov. 2010.*

(Continued)

*Primary Examiner* — Sarah A Slifka
*Assistant Examiner* — Brent Thomas
(74) *Attorney, Agent, or Firm* — Bacon & Thomas, PLLC

(57) ABSTRACT

An electrolyte for electrochemical device and the electrochemical device thereof. The electrolyte comprises 9.95~19.95 wt % of a salt; 80.0~90.0 wt % of a non-aqueous solvent; 0.05~10.00 wt % of an additive comprising a compound represented by below formula (I) or (II):

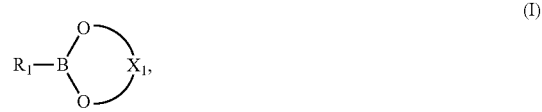

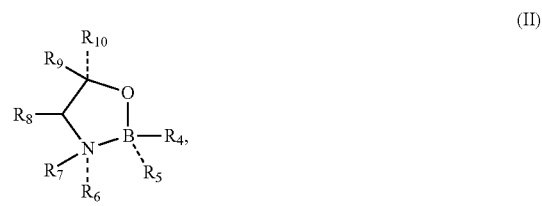

wherein X1, R1, and R4~R10 is defined as herein. Besides, the present invention also provides a method for enhancing cycle life of electrochemical device which accomplished by adding above additive to an electrolyte of electrochemical device.

9 Claims, 6 Drawing Sheets

(51) Int. Cl.
*C07F 5/02* (2006.01)
*H01M 10/0525* (2010.01)

(56) References Cited

U.S. PATENT DOCUMENTS

2006/0210883 A1   9/2006  Chen et al.
2007/0072085 A1*  3/2007  Chen et al. .................... 429/324
2009/0197161 A1*  8/2009  Nakamura .................... 429/158

OTHER PUBLICATIONS

X. Sun, H. S. Lee, X.-Q. Yang, and J. McBreen, "Using a Boron-Based Anion Receptor Additive to Improve the Thermal Stability of $LiPf_6$-Based Electrolyte for Lithium Batteries", *Electrochemical and Solid-State Letters*, 5 (11) A248-A251.

Xuehui Sun, Hung Sui Lee, Xiao-Qing Yang, and James McBreen, "The Compatibility of a Boron-Based Anion Receptor with Carbon Anode in Lithium-Ion Batteries", *Electrochemical and Solid-State Letters*, 6 (2) A43-A46 (2003).

Zonghai Chen and K. Amine, "Tris(pentafluorophenyl) Borane as an Additive to Improve the Power Capabilities of Lithium-Ion Batteries", *Journal of The Electrochemical Society*, 153 (6) A1221-A1225 (2006).

\* cited by examiner

ELECTROLYTE FOR ELECTROCHEMICAL DEVICE AND THE ELECTROCHEMICAL DEVICE THEREOF

BACKGROUND OF THE INVENTION

1. Field of the Invention

The present invention relates to an electrolyte for electrochemical device, and more particularly to an electrolyte for electrochemical device comprising a boron-based additive.

2. Description of the Related Art

Nowadays, there is a tendency towards lighter, thinner, shorter, and smaller in electronic, information, and biomedical equipment and instrument, so it is also expected that the batteries for the same can have advantages of smaller volume, and higher storage capacity and discharge capacity able to maintained after use for long time and thereby the relevant academic circles and industries gradually pay much attention to lithium ion batteries meeting these requirements.

The major parts of lithium ion batteries comprises a positive electrode made from positive electrode material, an electrolyte, a separator, and a negative electrode, wherein said positive electrode material generally is lithium cobalt oxides, lithium nickel oxides, or lithium manganese oxides. The principle of lithium ion batteries, in sum, is charge/discharge reaction performed by insertion and extraction of Li ions between positive and negative electrodes. Said charge/discharge reaction can be concluded as the following equations, in which M is Co, Ni, or Mn, and the reaction proceeds to the right during charge and to the left during discharge.

Reaction at positive electrode: 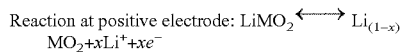
$MO_2 + xLi^+ + xe^-$

Reaction at negative electrode: $C_6 + xLi^+ + xe^-$
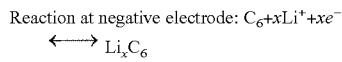 $Li_xC_6$

Overall reaction: 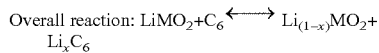 $Li_{(1-x)}MO_2 + Li_xC_6$

Lithium ion batteries have the advantages of lighter mass, higher density of energy, better cycle property, and higher electric power, so they are gradually applied to production requiring higher electric power, such as power tool or electric vehicle. In the consideration to the safety and cost required by batteries as sources of powering electric vehicles, lithium iron phosphate is just like cynosure for positive electrode material for lithium ion battery; however, the degradation of the performance of the lithium iron phosphate as a positive electrode material is quick under higher temperature so that the application of the lithium iron phosphate is restricted that is a problem which all companies extremely desires to solve.

U.S. Pat. No. 6,352,798B1 disclosed the effect of phenyl boron-based compound as an additive on enhancement of the conductivity of electrolyte. The conductivities of three electrolytes obtained by adding a phenyl boron-based compound to $LiCF_3COOLi$, $LiC_2F_5COOLi$, and LiF, respectively, in DMC at a concentration ratio of 1:1 were measured. It was found that the conductivity of the electrolyte increased with the increase of the added concentration of the phenyl boron-based compound, which was not affected by the sort of lithium salts. The result apparently indicated that all of phenyl boron-based compound have the same effect on any of lithium salts. The effect was that the conductivity of the electrolyte was enhanced by enhancement of dissociation of lithium salt.

US publication patent 20060210883A1 disclosed the effect of borane-based additives added to electrolytes in different weight percentage on impedances of the lithium ion batteries. 0, 1, 3, and 5 wt % of borane-based additives were added to 1.2 M $LiPF_6$ in EC/PC/DMC (1:1:3) and then used with anode composed of $Li_{1+x}[Ni_{1/3}Co_{1/3}Mn_{1/3}]_{0.9}O_2$ and natural graphite wrapped by carbon to obtain four batteries. After test, it was found that the interfacial impedance of the batteries was obviously enhanced when the added amount of said additive was achieved to 5 wt %. That was because the borane-based additive was involved to the formation of SEI films and contributed to dissolution of LiF during formation of SEI films and thereby improved the transportation of Li ions between SEI films. The result of cycle test at 55° C. also showed that the battery with less than 3 wt % of borane-based additive had better cycle life and maximal discharge power, which implied that the battery with excess added amount of borane-based additive in the electrolyte had higher interfacial impedance and discharge capacity thereof was also decreased.

*Journal of The Electrochemical Society*, 153 (6) (2006) A1221-A1225 disclosed that the discharge power of the battery composed of $Li_{1+x}[Ni_{1/3}Co_{1/3}Mn_{1/3}]_{0.9}O_2$ and natural graphite wrapped by carbon can be improved by applying Tris(pentafluorophenyl)borane (TPFPB) as an additive to electrolyte containing 1.2 M $LiPF_6$ in EC/PC/DMC (1:1:3) since TPFPB as an additive would induce the salt in the electrolyte to completely dissociate into cations and anions to enhance the conductivity of the electrolyte. Moreover, said additive can also reduce the production of LiF in the electrolyte, wherein said LiF is not good for the mobility of Li ions and electrons. Because free Li ion in the electrolyte would be reduced by the existence of LiF in the electrolyte, which extremely affected on the conductivity of the electrolyte, so TPFPB as an additive can assist completely dissociation of salt into cation and anion ions.

*Electrochemical and solid-State*, 5 (11) (2002) A248-A251 disclosed TPFPB as an additive. $LiPF_6$ can be completely dissociated into $LiF^+$ and $PF^-$ by adding 0.1M TPFPB to 1M $LiPF_6$ in EC/DMC (1:1) to reduce the formation of LiF and $PF_5^-$ and thereby prevent $PF_5^-$ from reacting with trace amount of water in the electrolyte to produce HF. Because of avoiding the product of HF corroding $LiMn_2O_4$ as a positive electrode material, the electrochemical stability and cycle property at 55° C. of the positive electrode material can be remarkably improved.

*Electrochemical and solid-State*, 6 (2) (2003) A43-A46 disclosed TPFPB as an additive. 0.1 M TPFPB was added to an electrolyte containing 1 M $LiPF_6$ in EC/DMC (1:1) and then charged and discharged to form a SEI film on the surface of the carbonaceous material (MCMB) as a negative electrode. Since TPFPB as an additive was present in the electrolyte, the stability of the SEI film can be maintained when carbonaceous material was cycled for long time. Besides, TPFPB as an additive contributed to completely dissolution of LiF, so SEI film still stably existed under higher temperature and the lithium ion batteries comprising the combination of $Li_{0.80}Co_{0.15}Al_{0.05}O_2$ with MCMB had higher capacity and longer cycle property.

In general, the above-mentioned additives had high molecular weight and poor solubility in the organic electrolytes, and would combine with anions in the electrolyte to form bulky molecules, thereby lowering ion mobility and affecting charge/discharge property at higher rate. However, the additive of the present invention has not only better solubility, but also less effect upon ion mobility. Moreover, the additive disclosed in the present invention has a lower cost than TPFPB and better property of discharge rate and is able to effectively improve the performance of the positive electrode material under higher temperature, so it is helpful to apply lithium ion batteries to electric vehicle, thereby facilitating the development of the industries related to electric vehicle.

SUMMARY OF THE INVENTION

In view of the disadvantages of conventional technology, one object of the present invention is to effectively improve the cycle property of lithium ion battery at higher temperature without increasing process complexity, which is accomplished by an electrolyte additive with higher electrochemical stability, less added amount, and the property helpful to improve the cycle property of lithium ion battery at higher temperature.

To achieve the above objects, the present invention provides an electrolyte for an electrochemical device, comprising 9.95-19.95 wt % of a salt, 80.0-90.0 wt % of a non-aqueous solvent, and 0.05-10.00 wt % of an additive comprising a compound represented by formula (I) or (II):

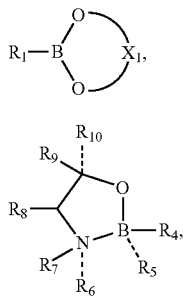

wherein $X_1$ is C2-C3 alkylene or a residue having below formula (III):

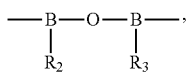

in which $R_1$ is unsubstituted or substituted phenyl, pyridyl, C2-C10 alkenyl, or C1-C3 alkoxy;

$R_2$ and $R_3$ are independently C1-C3 alkyl or C1-C3 alkoxy;

$R_4$ is C1-C3 alkyl or C1-C3 alkoxy;

$R_5$ is empty orbital or $R_5$ together with $R_6$, and the nitrogen atom and the boron atom to which $R_5$ and $R_6$ are linked is five-membered or six-membered ring having lactone structure;

$R_6$ is lone pair or $R_6$ together with $R_5$, and the boron atom and the nitrogen atom to which $R_5$ and $R_6$ are linked is five-membered or six-membered ring having lactone structure;

$R_7$ is C1-C3 alkyl or $R_7$ together with $R^8$, and the nitrogen atom and the carbon atom to which $R_7$ and $R_8$ are linked is five-membered or six-membered heterocyclic ring;

$R_8$ is hydrogen or $R_8$ together with $R_7$, and the carbon atom and the nitrogen atom to which $R_7$ and $R_8$ are linked is five-membered or six-membered heterocyclic ring;

$R_9$ and $R_{10}$ are independently hydrogen, C1-C3 alkyl, phenyl or oxo, provided that when one of $R_9$ and $R_{10}$ is oxo, the other is absent.

In a preferable embodiment, the salt is present in an amount of 11.0-12.0 wt %.

In a preferable embodiment, the additive is present in an amount of 0.2-5.0 wt %.

In a preferable embodiment, the salt is $LiPF_6$, $LiBF_4$, $LiN(CF_3SO_2)_2$, $LiCF_3SO_3$, or a mixture of the above.

In a preferable embodiment, the non-aqueous solvent is carbonates, furans, ethers, thioethers, nitriles, or a mixture of the above.

In a preferable embodiment, the non-aqueous solvent is ether polymers, polymethacrylate polymers, polyacrylate polymers, fluoropolymers, or combination thereof.

In a preferable embodiment, the compound represented by formula (I) is:

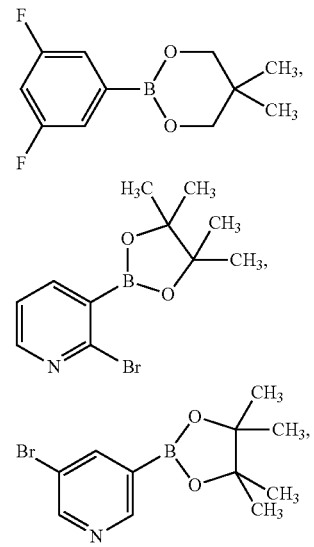

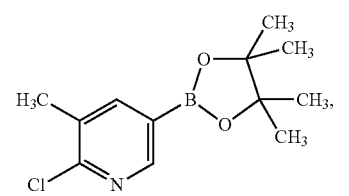

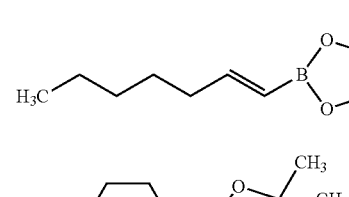

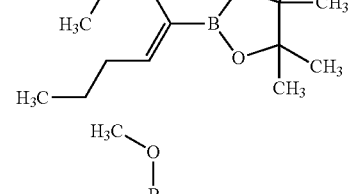

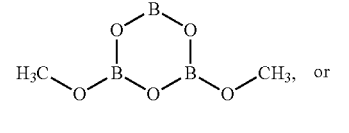

or

-continued

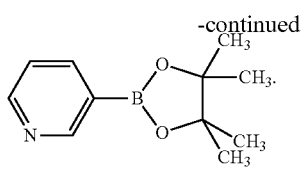

In a preferable embodiment, the compound represented by formula (II) is:

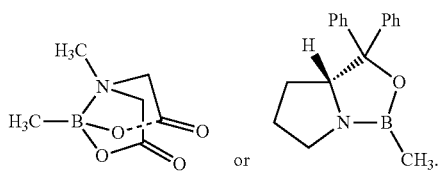

The present invention also provides an electrochemical device, comprising a positive electrode, a negative electrode, and the electrolyte of the present invention.

In a preferable embodiment, the electrochemical device is a lithium ion secondary battery.

Yet the present invention provides a method for enhancing cycle property of electrochemical device, comprising adding an additive comprising a compound represented by formula (I) or (II) to an electrolyte of electrochemical device.

From above, the electrolyte for an electrochemical device of the present invention comprises a novel boron-based (such as Borane- or Borate-based) additive. By means of the additive, the cycle property of the conventional lithium ion batteries can be improved.

DETAILED DESCRIPTION OF THE PREFERRED EMBODIMENTS

Figure 1:
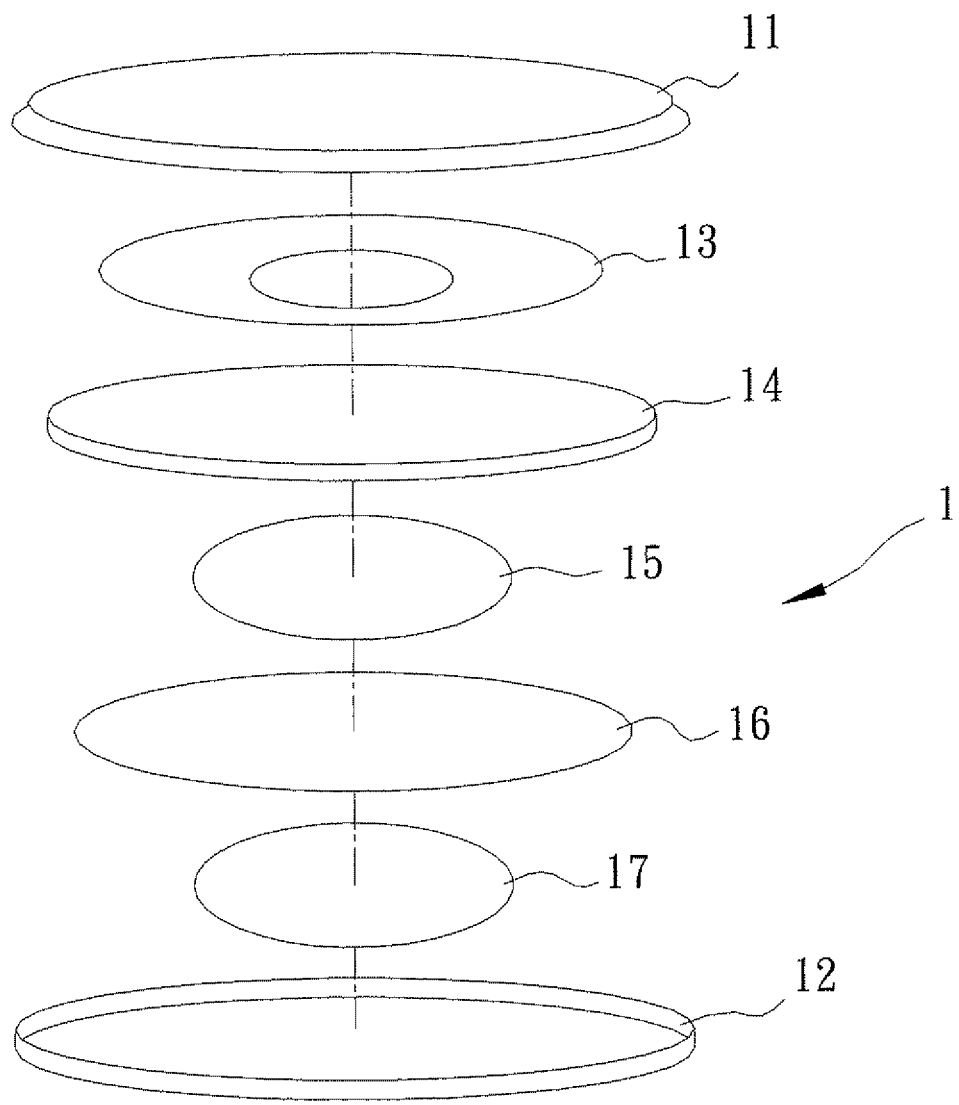
FIG. 1 is an exploded view schematically showing each unit of a lithium ion battery and the positional relations thereof.

The present invention provides an electrolyte for an electrochemical device that is different from the conventional electrolyte for an electrochemical device, containing a novel boron-based additive. By means of said additive, a lithium ion battery having a better cycle property than the conventional lithium ion battery can be provided.

The electrolyte for an electrochemical device of the present invention comprises 9.95-19.95 wt % of a salt, 80.0-90.0 wt % of a non-aqueous solvent, and 0.05-10.00 wt % of an additive comprising a compound represented by formula (I) or (II);

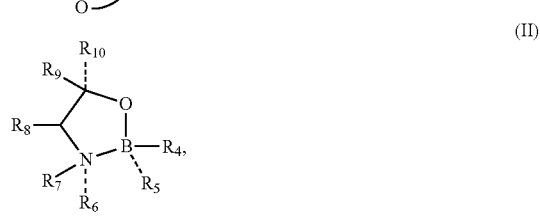

wherein $X_1$ is C2-C3 alkylene or a residue having below formula (III):

in which $R_1$ is unsubstituted or substituted phenyl, pyridyl, C2-C10 alkenyl, or C1-C3 alkoxy;

$R_2$ and $R_3$ are independently C1-C3 alkyl or C1-C3 alkoxy;

$R_4$ is C1-C3 alkyl or C1-C3 alkoxy;

$R_5$ is empty orbital or $R_5$ together with $R_6$, and the nitrogen atom and the boron atom to which $R_5$ and $R_6$ are linked is five-membered or six-membered ring having lactone structure;

$R_6$ is lone pair or $R_6$ together with $R_5$, and the boron atom and the nitrogen atom to which $R_5$ and $R_6$ are linked is five-membered or six-membered ring having lactone structure;

$R_7$ is C1-C3 alkyl or $R_7$ together with $R_9$, and the nitrogen atom and the carbon atom to which $R_7$ and $R_8$ are linked is five-membered or six-membered heterocyclic ring;

$R_8$ is hydrogen or $R_8$ together with $R_7$, and the carbon atom and the nitrogen atom to which $R_7$ and $R_8$ are linked is five-membered or six-membered heterocyclic ring;

$R_9$ and $R_{10}$ are independently hydrogen, C1-C3 alkyl, phenyl or oxo, provided that when one of $R_9$ and $R_{10}$ is oxo, the other is absent.

Specifically, the compound represented by formula (I) of the present invention is:

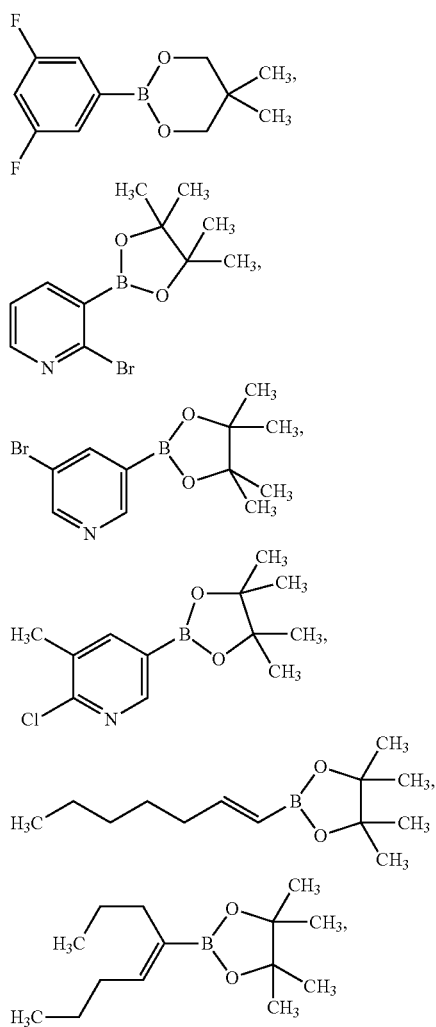

-continued

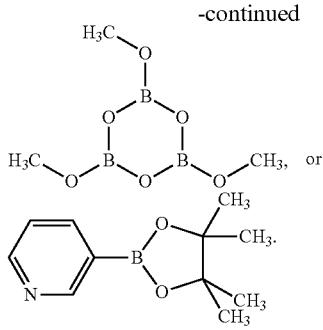

Specifically, the compound represented by formula (II) of the present invention is:

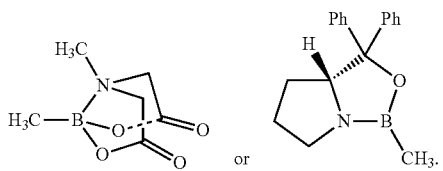

Based on convenient sake, the abbreviated names of the aforesaid ten compounds are listed in Table 1.

TABLE 1 list of the abbreviated name and the corresponding structure thereof

| abbreviated name | structure of additive |
| --- | --- |
| DANGE | 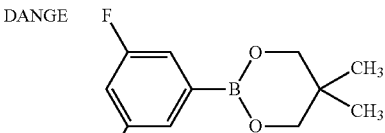 |
| BBAPE | 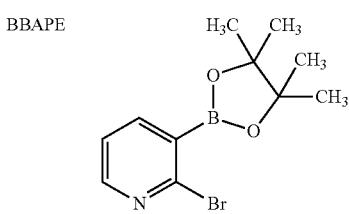 |
| BPAPE | 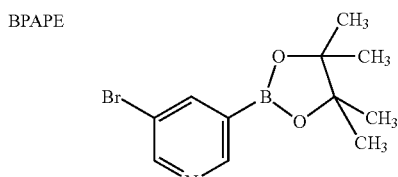 |
| CMBAPE | 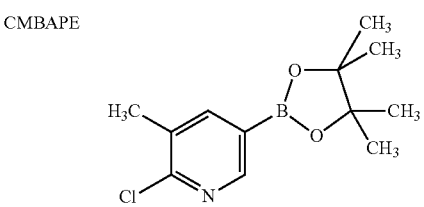 |

TABLE 1-continued list of the abbreviated name and the corresponding structure thereof

| abbreviated name | structure of additive |
|---|---|
| HYAPE | (E)-2-(hex-1-en-1-yl)-4,4,5,5-tetramethyl-1,3,2-dioxaborolane structure |
| OYAPE | 2-(3-ethylhex-3-en-3-yl)-4,4,5,5-tetramethyl-1,3,2-dioxaborolane-type structure |
| TMOB | trimethoxyboroxine (cyclic B-O-B-O-B-O ring with three OCH$_3$ groups) |
| PAPE | 2-(pyridin-3-yl)-4,4,5,5-tetramethyl-1,3,2-dioxaborolane |
| MAME | N-methyl-B-methyl boron-containing cyclic structure with carbonyls |
| MCO | pyrrolidine-fused oxazaborolidine with Ph, Ph and CH$_3$ substituents |

In the present invention, the amount of each of components in the electrolyte can be modified in accordance with the practical application, but the salt is preferably present in an amount of 11.0~12.0 wt %; the additive is preferably present in an amount of 0.2~5.0 wt %. With respect to the non-aqueous solvent, its amount can be changed in response to the amount of the other components in the electrolyte, as long as the total amount of the non-aqueous solvent plus other components in the electrolyte is 100 wt %. That is to say, the non-aqueous solvent is used as complement of the electrolyte to 100 wt %; however, generally speaking, the non-aqueous solvent is preferably present in an amount of 85.8-88.6 wt %.

The salt suitable for the present invention is common lithium salts in the art, comprising LiPF$_6$, LiBF$_4$, LiN(CF$_3$SO$_2$)$_2$, LiCF$_3$SO$_3$, or combination thereof. Preferably, the salt is selected from LiPF$_6$, LiBF$_4$, or combination thereof.

The form of the non-aqueous solvent in the electrolyte of the present invention may be, but not limited to, solid, gel, or liquid. As for the liquid non-aqueous solvent, it may be selected from solvents commonly used in the art, for example, carbonates (such as ethylene carbonate, propylene carbonate, dimethyl carbonate, diethyl carbonate, or methylethyl carbonate), furans (such as tetrahydrofuran), ethers (such as diethyl ether), sulfides (such as methyl-sulfolane), nitriles (such as acetonitrile or propanenitrile), or combination thereof.

With respect to solid non-aqueous solvent, it may be polymer compound. For example, ether polymers (such as uncrosslinked or crosslinked polyethyleneoxide), polymethacrylate polymers, polyacrylate polymers, fluoropolymers (such as polyvinylidene (PVDF) or vinylidene fluoride-hexafluoro propylene copolymer), or combination thereof may be selected.

There are no particular limitations on the kind of the salt. For example, lithium salt (such as LiPF$_6$, LiBF$_4$, LiN(CF$_3$SO$_2$)$_2$, LiCF$_3$SO$_3$, or combination thereof) may be used.

The electrolyte of the present invention may be obtained by dissolving a salt and an additive into the aforesaid liquid non-aqueous solvent or dissolving a salt and an additive into the aforesaid liquid non-aqueous solvent separately and then mixing each other. When the non-aqueous solvent is solid, the electrolyte of the present invention may be obtained by utilizing an organic solvent (such as alkanes, ketones, aldehydes, alcohols, ethers, benzene, toluene, xylene, paraffin, or combination thereof) to dissolve a salt, additive, and the non-aqueous solvent and uniformly mixing each other and then vaporizing the organic solvent by heat.

The electrolyte is applied to a conventional electrochemical device to obtain an electrochemical device different from the conventional electrochemical device. In other words, the present invention also provides an electrochemical device comprising a positive electrode, a negative electrode, and the electrolyte of the present invention.

In a preferable embodiment, the electrochemical device is a lithium ion secondary battery.

The structure of the lithium ion secondary battery is illustrated in detail hereinafter; however, it should be understood that those descriptions are not used for limiting the lithium ion secondary battery of the present invention.

As shown in FIG. 1, a lithium ion secondary battery 1 comprises an upper cap 11 and lower cap 12 that are mutually connected to jointly define an enclosed space (not shown in FIG. 1). The lithium ion secondary battery 1 further comprises a spring washer 13, a stainless steel disc 14, a negative electrode sheet 15, a separator 16, and a positive electrode sheet 17 that are arranged in the series of order toward the direction of lower cap 12. Besides, the lithium ion secondary battery 1 also comprises an electrolyte (not shown in FIG. 1) loaded inside the enclosed space.

It is emphasized here that the lithium ion secondary battery of the present invention can be used with a spring washer made of any exemplified substance or any material that is well known in the industry at present, a stainless steel disc, a negative electrode sheet, a separator, and a positive electrode sheet. Modification of kinds, manufacturing methods, used amounts and so on of the aforesaid parts of the battery are well known in the art and are also able to be handled by one skilled in the art in accordance with expertises and requirements, so they are only slightly described in the present invention.

In the method for manufacturing the positive electrode sheet, the kinds, used amounts, shapes, and so on of the positive electrode material, the conductive material, the binder, the solvent used, and current collector material may be modified by one skilled in the art in accordance with expertises and requirements. For example, in general practical operation, the raw material of the positive electrode material is transition metal oxides of lithium such as LiM$_{(1-x)}$ $M'_xO_2$ ($x \leq 1$) or $LiM_{(2-y)}M'_yO_4$ ($y \leq 2$), in which each of M and M' is selected from the group consisting of Ti, V, Cr, Mn, Fe, Co, Ni, Zn, Al, and Sn, and at least one of M and M' is a transition metal. The method for manufacturing the positive electrode may refer to the content of chapter 3 in Lithium ion batteries, Central South University, China, (2002). In addition, the raw material of the positive electrode material may include two or more kinds of transition metal oxides of lithium, or may further include other chemical substances (such as lithium carbonate) for the requirement of the design of battery. Besides, the positive electrode sheet may also be a sheet of lithium foil. The conductive material may be selected from carbon black or carbon nanofiber. In some cases, the conductive material may not be added; however, if the conductive material is added, the used amount thereof is usually about 0.1 wt %-10 wt % by the total weight of the positive electrode material, conductive material, and binder. As to the thickness of the coating layer (i.e. positive electrode material), it is preferably 20~50 μm.

As to the above binder, it is preferably a substance with chemical stability and electrochemical stability under higher pressure in the electrolyte. In general, the amount of the binder is preferably 1 to 10 based on the weight of the positive electrode material. The binder may be selected from fluoropolymers (such as polyvinylidene fluoride (PVDF) or polytetrafluoroethylene commonly used in the industry), polyolefin (such as polyethylene (PE), polyvinyl alcohol (PVA), styrene-butadiene rubber (SBR) commonly used in the industry), or celluloses (such as carboxymethylcellulose commonly used in the industry). The mixture of the above may also be used.

As for the solvent for manufacturing the positive electrode sheet, water, N-methyl pyrrolidone, dimethylformamide, alcohols (such as ethanol or isopropanol), or combination thereof may commonly be used. Among those solvents, water and N-methylpyrrolidone are more commonly used and N-methylpyrrolidone is most commonly used. There have been a lot of modifications with regard to the manipulation of the kinds and amounts used of the solvent. They are well known in the art and are also able to be handled by one skilled in the art in accordance with expertises and requirements, so there is no particular description in the present invention.

The current collector material as above may be made of aluminum. The shape of current collector material is particularly not limited, which is usually thin shape such as foil or mesh. The size of current collector material (such as length, width, thickness, or weight) depends on the size of desired prepared negative electrode sheet and the thickness of current collector material is preferably 5 to 20 μm.

The separator 16 is used for insulation to prevent short circuit of the battery, thereby enhancing safety and allowing ions to flow between positive and negative electrolyte sheets. The form of the suitable separator for the present invention is not limited particularly; for example, it is in the form of solid (such as nonwoven fabric or porous membrane) or gel commonly used in the art. Most of separators are made of polyolefines. Among polyolefines, polypropylene/polyethylene (PP/PE) or polypropylene/polyethylene/polypropylene (PP/PE/PP) is commonly used and polypropylene/polyethylene/polypropylene (PP/PE/PP) is more commonly used.

As mentioned above, the present invention focuses on improving the disadvantage of the conventional lithium ion batteries that is poor cycle property by addition of the boron-based additive, so the present invention yet provides a method for enhancing cycle property of electrochemical device, comprising adding an additive comprising a compound represented by formula (I) or (II) to an electrolyte of electrochemical device.

Before the compound represented by formula (I) or (II) is added, the concentration of the salt in the electrolyte of the electrochemical device is preferably 0.1~1.5M, more preferably 0.5~1.2M.

The additive may be added directly to the electrolyte or be dispersed into non-aqueous solvent and then be added to the electrolyte. Generally speaking, it is preferable that the additive is added in a concentration of 0.01M~4.00M.

The examples of this invention are provided hereinafter; however, these examples are not used for limit the present invention. Any amendments and modifications can be made by those skilled in the art without departing the spirit and scope of the present invention. The scope of the present invention is defined by the appended claims.

EXAMPLE

Preparation of Electrolyte

Chemicals
1. Ethylene Carbonate (EC) with the purity of 99% manufactured by Germany Merck company
2. Dimethyl Carbonate (DMC) with the purity of 99% manufactured by Germany Merck company
3. Salt ($LiPF_6$) with the purity of 99% manufactured by Morita Chemical company
4. Boron-based additive provided from Aldrich Preparation Method:
EC was mixed with DMC in a weight ratio of 1:1. After dissolution, 11.8 wt % of salt ($LiPF_6$) based on molarity was added to the mixture of EC and DMC (1:1), and then stirred by magnet for complete dissolution. The resulted solution without boron-based additive was used as an electrolyte of comparative example 1.

0.057 g of 3,5-difluorobenzeneboronic acid neopentyl glycol ester (DANGE) as a additive was uniformly mixed with 10 g of the electrolyte of comparative example 1 in a glove box with moisture content and oxygen content of less than 10 ppm to obtain a electrolyte with DANGE content of 0.56 wt % as the example 1, which is the electrolyte of the present invention.

The electrolytes of examples 2-22 were prepared as that of the example 1 except for the concentrations or kinds of additives. Each of the abbreviated names and the corresponding structures of the additives used in the examples were listed in above Table 1 and each of the additives and the concentrations used in the examples was listed in Table 2.

[Preparation of Lithium Ion Secondary Battery]:
Materials
1. Positive Electrode Sheet:
   (1) Lithium iron phosphate powder manufactured by Changyuan company
   (2) Carbon black (Super-P) manufactured by Timcal company as a conductive material
   (3) N-methyl-2-tetrahydropyrrolidone (NMP, $C_5H_9NO$) with the purity of 99.5% manufactured by ISP Electronics Inc. as a solvent
   (4) PVDF (6020) with the molecular weight of about 304,000 manufactured by Solvay company as a binder
   (5) Oxalic acid with the purity of 99.0% manufactured by SHOWA company
   (6) Aluminum foil with the thickness of 15 μm manufactured by Nippon foil company as a current collector material 2. Other Parts of Battery:
  (1) Upper cap and lower cap manufactured by Lemon One Industrial Co., Ltd. Taiwan (2032)
  (2) Spring washer manufactured by Lemon One Industrial Co., Ltd. Taiwan
  (3) Stainless steel disc manufactured by Lemon One Industrial Co., Ltd. Taiwan
  (4) Separator made of PP/PE/PP manufactured by Celgard (Celgard 2300)
  (5) Lithium foil with the purity of 99.9% in the shape of disc having a diameter of 1.65 cm, manufactured by FMC as a negative electrode sheet 3. Electrolytes:
  (1) Electrolytes of the examples 1-22 and the comparative example 1

Preparation Method:

A positive electrode material (such as lithium iron phosphate powder) was blended with a conductive material (carbon black), a binder (PVDF), and oxalic acid at the ratio of 90.9:3:6:0.1 by weight to obtain a solid composition. Then, 57% by weight of solvent (NMP) based on said solid composition was added and well mixed to produce a slurry mixture. The slurry mixture was coated onto a current collector material in the form of foil (aluminum foil) and dried, and then pressurized and cut to produce the positive electrolyte sheet.

After that, the parts of battery and the electrolytes as mentioned above were prepared to assemble with the respective positive sheets in a glove box with moisture content and oxygen content of less than 10 ppm equipped with a battery capping machine, in which said glove box was manufactured from Unilab Mbraum company and had a model number of 150B-G. During the assembly of the batteries, the electrolytes were added and then capped by the battery capping machine for ensuring their closure. After that, the coin cells to be tested were obtained, respectively.

[Performance Test]:

Lithium ion secondary batteries prepared with the electrolytes of the examples and the comparative example were tested for the following performance tests.

[Initial Charge/Discharge Test]

Each of batteries was charged by charge/discharge tester (BAT-700S manufactured by AcuTech Systems Co., Ltd.) at constant current of 0.1 C until the instrument showed that the circuit voltage of the battery reached 4.2V to obtain the value of the first charge capacity of the battery. After 5 minutes, each of batteries was discharged at constant current with 0.1 C current until the circuit voltage reached 2.5V to obtain the value of the first discharge capacity of the battery. Subsequently, the irreversibility percentage of capacity of each of batteries was calculated from the following equation.

$$\text{irreversibility percentage}(\%) = \frac{\text{first charge capacity} - \text{first discharge capacity}}{\text{first charge capacity}} \times 100$$

The irreversibility percentage of capacity and the charge/discharge capacity (mAhg$^{-1}$) obtained from each of the examples and comparative example were all listed in Table 2.

TABLE 2 cycle property at 0.1 C charge/discharge at 25° C. or 60° C.

| operation method | additive | concentration [wt %] | 1$^{st}$ charge capacity [mAh g$^{-1}$] | 1$^{st}$ discharge capacity [mAh g$^{-1}$] | irreversibility [%] |
|---|---|---|---|---|---|
| comparative example 1 | none | | 142 | 116 | 18.3 |
| example 1 | DANGE | 0.56 | 139 | 132 | 5.0 |
| 2 | DANGE | 1.12 | 141 | 131 | 7.1 |
| 3 | DANGE | 2.21 | 143 | 134 | 6.3 |
| 4 | TMOB | 0.43 | 147 | 137 | 6.8 |
| 5 | TMOB | 0.86 | 141 | 126 | 10.6 |
| 6 | TMOB | 1.71 | 140 | 133 | 5.0 |
| 7 | PAPE | 0.51 | 147 | 137 | 6.8 |
| 8 | PAPE | 1.01 | 143 | 128 | 10.5 |
| 9 | PAPE | 2.01 | 142 | 126 | 11.2 |
| 10 | MAME | 0.36 | 141 | 126 | 10.6 |
| 11 | MAME | 0.72 | 140 | 128 | 8.6 |
| 12 | MAME | 1.44 | 151 | 134 | 11.3 |
| 13 | MCO | 0.69 | 139 | 132 | 5.0 |
| 14 | MCO | 1.37 | 138 | 126 | 8.7 |
| 15 | MCO | 2.70 | 140 | 129 | 7.9 |
| 16 | CMBAPE | 1.25 | 136 | 123 | 9.5 |
| 17 | CMBAPE | 2.47 | 142 | 131 | 7.7 |
| 18 | OYAPE | 0.59 | 139 | 128 | 7.9 |
| 19 | OYAPE | 1.18 | 144 | 133 | 7.7 |
| 20 | OYAPE | 2.33 | 133 | 122 | 8.3 |
| 21 | BBAPE | 0.69 | 140 | 130 | 7.6 |
| 22 | BBAPE | 1.47 | 143 | 131 | 8.3 |

[100 Times Charge/Discharge Test at 1 C Rate]

The test was carried out by the following procedure. Each of the batteries according to the examples and comparative example 1 was charged and discharged for three cycles at 0.1 C and charge/discharge test was then conducted at 1 C rate at room temperature (25° C.) and higher temperature (60° C.), respectively, for 100 times. The cycle property was calculated by the combination of the following formula with the 10$^{th}$, 50$^{th}$, and 100$^{th}$ discharge capacities. All of the calculated cycle properties were listed in Table 3.

$$\text{cycle property}(\%) = \frac{Nth \text{ discharge capacity at } 1C \text{ rate}}{1st \text{ discharge capacity}} \times 100$$

Table 3 listed the tenth, fiftieth, and hundredth discharge capacities and hundredth cycle properties at 1 C rare at different temperatures of all of examples and comparative example, wherein the tenth, fiftieth, and hundredth discharge capacities and hundredth cycle property were exhibited by 10$^{th}$, 50$^{th}$, and 100$^{th}$ discharge capacities and 100$^{th}$ cycle property in Table 3, respectively.

TABLE 3 cycle property at 1 C rate of charge/discharge at 25° C. or 60° C.

| operation method | additive | concentration [wt %] | temperature [° C.] | $1^{st}$ discharge capacity [mAh g$^{-1}$] | $10^{th}$ discharge capacity [mAh g$^{-1}$] | $100^{th}$ discharge capacity [mAh g$^{-1}$] | $100^{th}$ cycle property [%] |
|---|---|---|---|---|---|---|---|
| comparative example 1 | none | | 25 | 83 | 76 | 62 | 75 |
| | | | 60 | 118 | 84 | 23 | 20 |
| example 1 | DANGE | 0.56 | 25 | 96 | 85 | 62 | 65 |
| | | | 60 | 126 | 120 | 61 | 48 |
| 2 | DANGE | 1.12 | 25 | 107 | 95 | 80 | 75 |
| | | | 60 | 126 | 108 | 32 | 25 |
| 3 | DANGE | 2.21 | 25 | 115 | 103 | 85 | 74 |
| | | | 60 | 129 | 123 | 37 | 29 |
| 4 | TMOB | 0.43 | 25 | 118 | 104 | 77 | 65 |
| | | | 60 | 134 | 126 | 76 | 57 |
| 5 | TMOB | 0.86 | 25 | 109 | 95 | 74 | 68 |
| | | | 60 | 138 | 111 | 45 | 33 |
| 6 | TMOB | 1.71 | 25 | 112 | 95 | 54 | 48 |
| | | | 60 | 132 | 122 | 47 | 36 |
| 7 | PAPE | 0.51 | 25 | 105 | 93 | 68 | 65 |
| | | | 60 | 127 | 122 | 41 | 32 |
| 8 | PAPE | 1.01 | 25 | 95 | 83 | 59 | 62 |
| | | | 60 | 130 | 123 | 78 | 60 |
| 9 | PAPE | 2.01 | 25 | 97 | 90 | 69 | 71 |
| | | | 60 | 127 | 120 | 95 | 75 |
| 10 | MAME | 0.36 | 25 | 104 | 97 | 67 | 64 |
| | | | 60 | 137 | 122 | 43 | 31 |
| 11 | MAME | 0.72 | 25 | 94 | 83 | 53 | 56 |
| | | | 60 | 131 | 119 | 51 | 39 |
| 12 | MAME | 1.44 | 25 | 101 | 92 | 59 | 58 |
| | | | 60 | 136 | 132 | 66 | 48 |
| 13 | MCO | 0.69 | 25 | 111 | 101 | 81 | 72 |
| | | | 60 | 133 | 112 | 27 | 20 |
| 14 | MCO | 1.37 | 25 | 112 | 102 | 86 | 76 |
| | | | 60 | 127 | 110 | 28 | 22 |
| 15 | MCO | 2.70 | 25 | 117 | 106 | 84 | 72 |
| | | | 60 | 125 | 113 | 31 | 25 |
| 18 | OYAPE | 0.59 | 25 | 105 | 101 | 89 | 85 |
| | | | 60 | 148 | 126 | 18 | 12 |
| 19 | OYAPE | 1.18 | 25 | 113 | 107 | 92 | 81 |
| | | | 60 | 127 | 108 | 25 | 19 |
| 20 | OYAPE | 2.33 | 25 | 101 | 97 | 82 | 81 |
| | | | 60 | 108 | 91 | 34 | 31 |
| 21 | BBAPE | 0.69 | 25 | 119 | 112 | 38 | 31 |
| 22 | BBAPE | 1.47 | 25 | 124 | 122 | — | — |

In addition, the data in the Table 3 were collected to exhibit in FIGS. 2-7 to clearly express the difference in cycle life under different conditions. The symbols of the comparative example 1 and each of examples were listed in Table 4.

TABLE 4 conversion table of symbols

Figure 2:
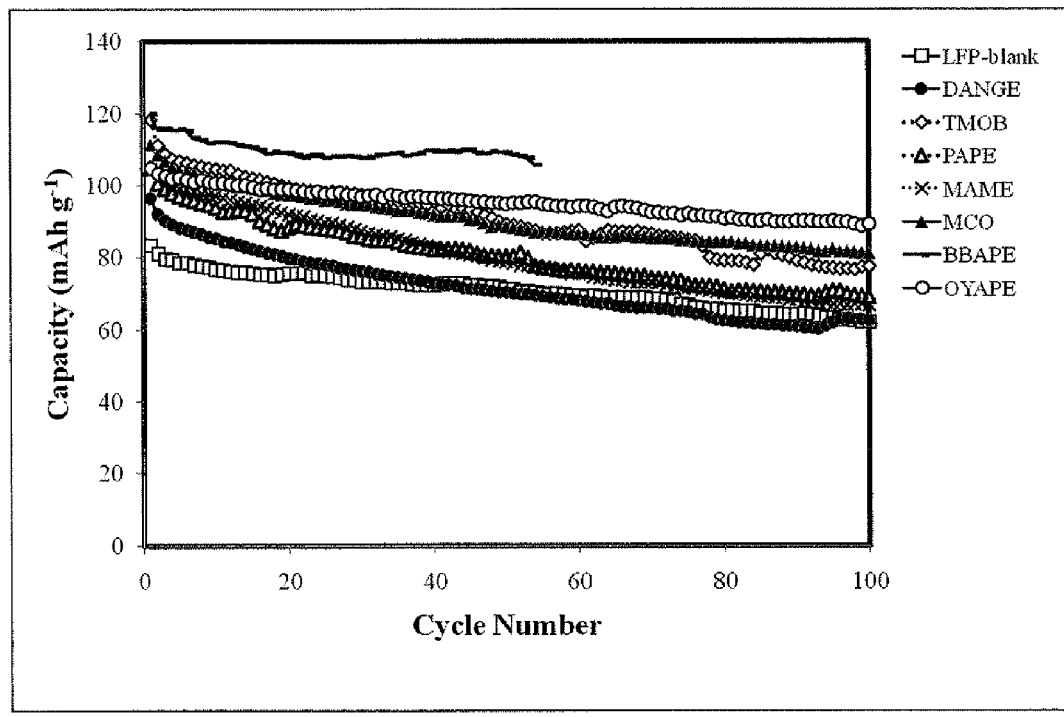
FIG. 2 is a chart of cycle life showing each of the discharge capacities of the batteries according to the comparative example 1 and the examples 1, 4, 7, 10, 13, 18, and 21 obtained by charging and discharging at 1 C rate at room temperature (25° C.) for 100 times, in which the meaning of each of the symbols is listed in Table 4.
Figure 3:
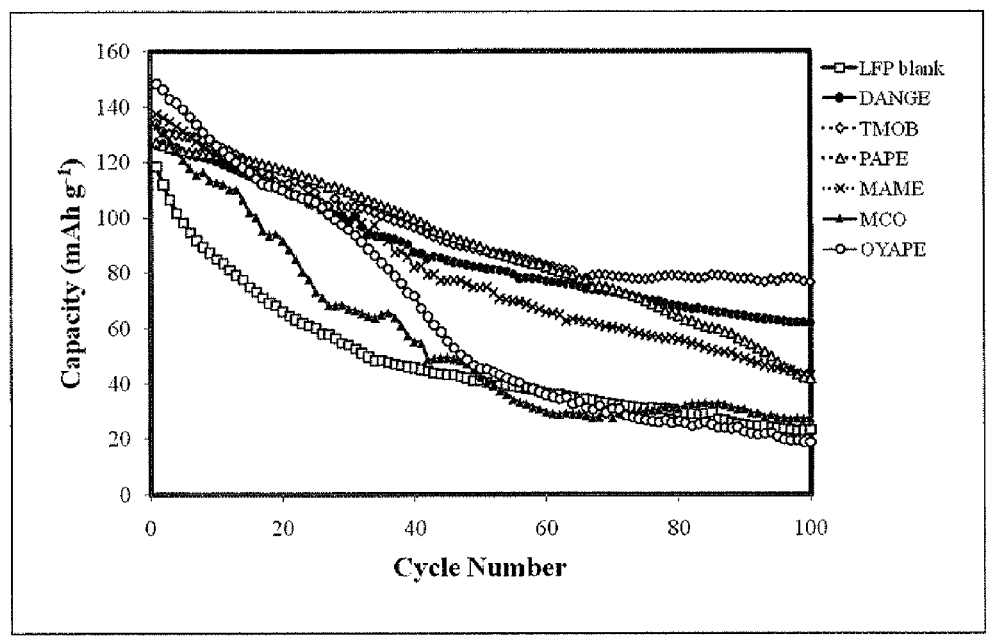
FIG. 3 is a chart of cycle life showing each of the discharge capacities of the batteries according to the comparative example 1 and the examples 1, 4, 7, 10, 13, and 18 obtained by charging and discharging at 1 C rate at higher temperature (60° C.) for 100 times, in which the meaning of each of the symbols is listed in Table 4.

| Figure | Symbol | Corresponding example or comparative example |
|---|---|---|
| FIG. 2 | □ | Comparative example 1 |
| | ● | Example 1 |
| | ◇ | Example 4 |
| | △ | Example 7 |
| | X | Example 10 |
| | ▲ | Example 13 |
| | ○ | Example 18 |
| | — | Example 21 |
| FIG. 3 | □ | Comparative example 1 |
| | ● | Example 1 |
| | ◇ | Example 4 |
| | △ | Example 7 |
| | X | Example 10 |
| | ▲ | Example 13 |
| | ○ | Example 18 |

TABLE 4-continued conversion table of symbols

Figure 4:
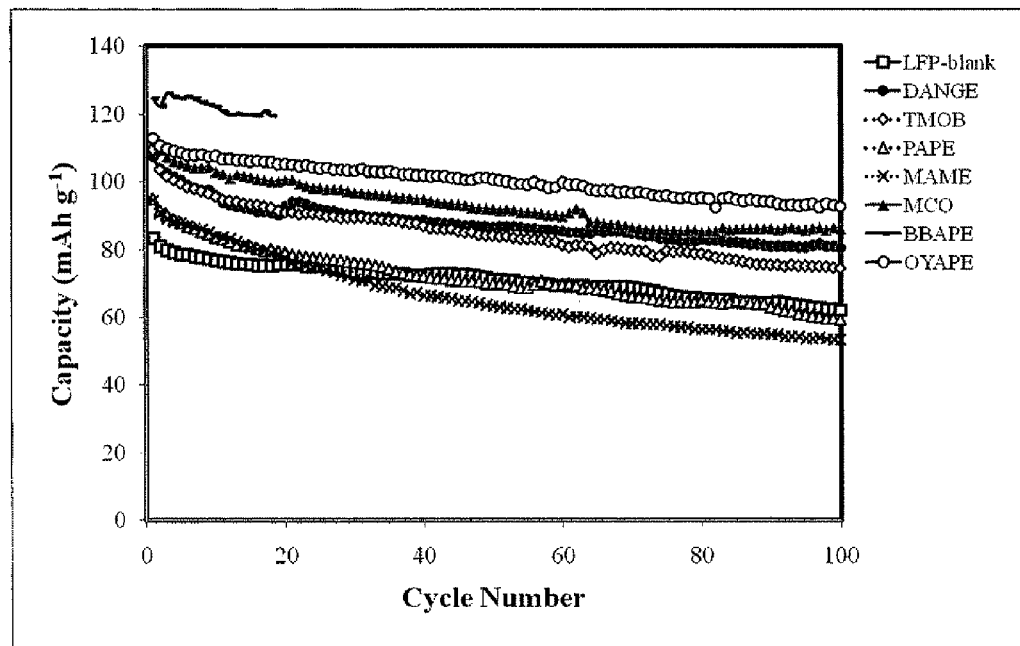
FIG. 4 is a chart of cycle life showing each of the discharge capacities of the batteries according to the comparative example 1 and the examples 2, 5, 8, 11, 14, 19, and 22 obtained by charging and discharging at 1 C rate at room temperature (25° C.) for 100 times, in which the meaning of each of the symbols is listed in Table 4.
Figure 5:
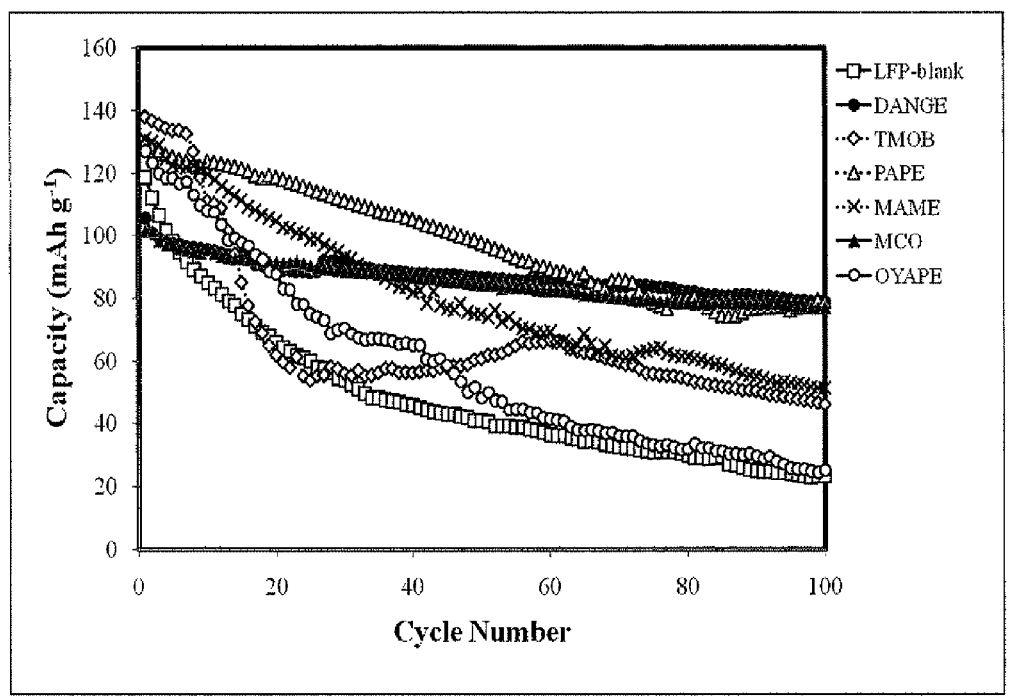
FIG. 5 is a chart of cycle life showing each of the discharge capacities of the batteries according to the comparative example 1 and the examples 2, 5, 8, 11, 14, 19, and 22 obtained by charging and discharging at 1 C rate at higher temperature (60° C.) for 100 times, in which the meaning of each of the symbols is listed in Table 4.
Figure 6:
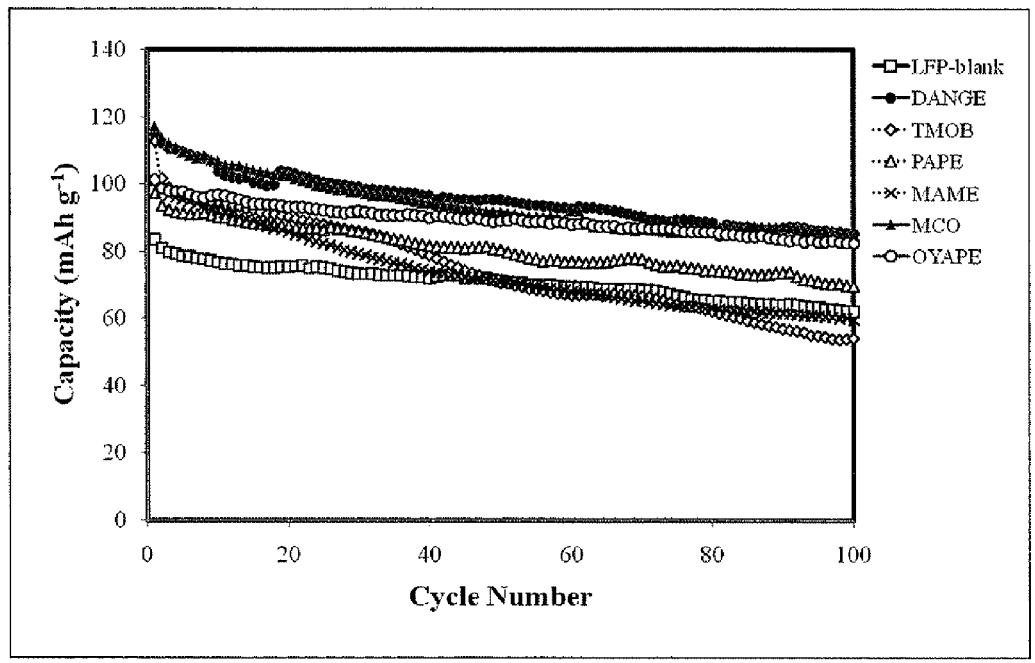
FIG. 6 is a chart of cycle life showing each of the discharge capacities of the batteries according to the comparative example 1 and the examples 3, 6, 9, 12, 15, and 20 obtained by charging and discharging at 1 C rate at room temperature (25° C.) for 100 times, in which the meaning of each of the symbols is listed in Table 4.

| Figure | Symbol | Corresponding example or comparative example |
|---|---|---|
| FIG. 4 | □ | Comparative example 1 |
| | ● | Example 2 |
| | ◇ | Example 5 |
| | △ | Example 8 |
| | X | Example 11 |
| | ▲ | Example 14 |
| | ○ | Example 19 |
| | — | Example 22 |
| FIG. 5 | □ | Comparative example 1 |
| | ● | Example 2 |
| | ◇ | Example 5 |
| | △ | Example 8 |
| | X | Example 11 |
| | ▲ | Example 14 |
| | ○ | Example 19 |
| FIG. 6 | □ | Comparative example 1 |
| | ● | Example 3 |
| | ◇ | Example 6 |
| | △ | Example 9 |
| | X | Example 12 |
| | ▲ | Example 15 |
| | ○ | Example 20 |

TABLE 4-continued conversion table of symbols

Figure 7:
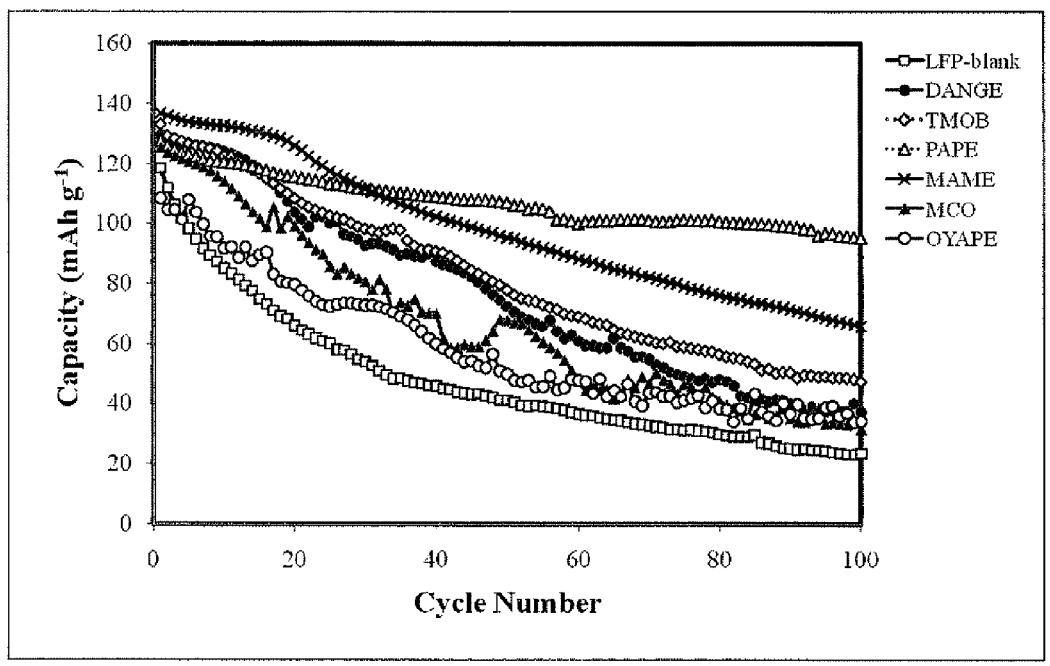
FIG. 7 is a chart of cycle life showing each of the discharge capacities of the batteries according to the comparative example 1 and the examples 3, 6, 9, 12, 15, and 20 obtained by charging and discharging at 1 C rate at higher temperature (60° C.) for 100 times, in which the meaning of each of the symbols is listed in Table 4.

| Figure | Symbol | Corresponding example or comparative example |
|---|---|---|
| FIG. 7 | □ | Comparative example 1 |
| | ● | Example 3 |
| | ◇ | Example 6 |
| | △ | Example 9 |
| | × | Example 12 |
| | ▲ | Example 15 |
| | ○ | Example 20 |

[Discharge Test at Different Rates]:

The test was carried out by the following procedure. Each of the batteries according to the examples and comparative example 1 was charged at 0.1 C rate and then discharged at various rates that are 0.1 C, 0.2 C, 0.5 C, 1 C, 2 C, and 5 C. All of discharge rates were performed for five times to obtain six kinds of the capacities of the batteries. That is to say, thirty capacities can be obtained. After that, the average and standard deviation of the five capacities obtained at each rate were calculated and then capacity percentage was calculated by using the average with the following equation. It should be noted that the average and standard deviation of the capacities at 0.1 C rate were calculated with capacities of the second to five cycles. The calculated results were shown in Table 5.

$$\text{capacity percentage}(\%) = \frac{\text{the average of discharge capacities at } nC \text{ rate}}{\text{the average of discharge capacities at } 0.1C \text{ rate for 2-5 cycles}} \times 100$$

Table 5 listed the average of discharge capacities (mAhg$^{-1}$), standard deviation, and capacity percentage at 0.1 C, 0.2 C, 0.5 C, 1 C, 2 C, or 5 C of all of examples and comparative example 1.

TABLE 5 the average of discharge capacities (mAhg$^{-1}$), standard deviation, and capacity percentage at 0.1 C, 0.2 C, 0.5 C, 1 C, 2 C, or 5 C

| operation method | | additive | additive [wt %] | 0.1 C | | | 0.5 C | | | 1 C | | | 2 C | | | 5 C | | |
|---|---|---|---|---|---|---|---|---|---|---|---|---|---|---|---|---|---|---|
| | | | | the average of capacities | Standard deviation | percentage | the average of capacities | Standard deviation | percentage | the average of capacities | Standard deviation | percentage | the average of capacities | Standard deviation | percentage | the average of capacities | Standard deviation | percentage |
| comparative example 1 | | none | | 128 | 0.29 | 100 | 110 | 1.14 | 86 | 93 | 0.61 | 73 | 78 | 0.32 | 61 | 42 | 1.61 | 32 |
| example | 1 | DANGE | 0.56 | 129 | 0.85 | 100 | 123 | 0.2 | 95 | 117 | 0.65 | 91 | 108 | 0.67 | 83 | 84 | 0.64 | 65 |
| | 2 | DANGE | 1.12 | 132 | 0.75 | 100 | 119 | 0.32 | 90 | 111 | 0.21 | 84 | 98 | 1.2 | 75 | 74 | 0.80 | 56 |
| | 3 | DANGE | 2.21 | 134 | 0.47 | 100 | 117 | 0.50 | 88 | 108 | 0.27 | 81 | 95 | 1.17 | 71 | 73 | 0.56 | 55 |
| | 4 | TMOB | 0.43 | 121 | 0.36 | 100 | 105 | 1.25 | 87 | 95 | 0.58 | 78 | 75 | 0.16 | 62 | 36 | 0.25 | 30 |
| | 5 | TMOB | 0.86 | 117 | 0.22 | 100 | 101 | 1.13 | 86 | 83 | 0.58 | 71 | 58 | 0.56 | 50 | 24 | 1.91 | 21 |
| | 6 | TMOB | 1.71 | 132 | 1.63 | 100 | 123 | 0.46 | 93 | 115 | 0.81 | 86 | 102 | 0.99 | 77 | 72 | 0.94 | 54 |
| | 7 | PAPE | 0.51 | 113 | 0.46 | 100 | 102 | 1 | 90 | 85 | 0.94 | 75 | 60 | 0.86 | 53 | 22 | 0.25 | 20 |
| | 8 | PAPE | 1.01 | 124 | 0.47 | 100 | 113 | 0.7 | 91 | 106 | 0.52 | 85 | 97 | 0.54 | 77 | 79 | 0.54 | 64 |
| | 9 | PAPE | 2.01 | 138 | 0.63 | 100 | 120 | 0.52 | 87 | 114 | 0.03 | 82 | 102 | 0.40 | 76 | 86 | 0.72 | 62 |
| | 10 | MAME | 0.36 | 125 | 0.66 | 100 | 116 | 0.27 | 92 | 110 | 0.33 | 88 | 102 | 0.34 | 81 | 86 | 0.41 | 69 |
| | 11 | MAME | 0.72 | 134 | 0.51 | 100 | 124 | 0.25 | 93 | 117 | 0.27 | 88 | 109 | 0.14 | 81 | 93 | 0.44 | 70 |
| | 12 | MAME | 1.44 | 129 | 0.24 | 100 | 118 | 0.19 | 92 | 112 | 0.20 | 87 | 104 | 0.50 | 81 | 87 | 0.35 | 67 |
| | 13 | MCO | 0.69 | 137 | 1.31 | 100 | 129 | 0.94 | 94 | 118 | 0.34 | 85 | 108 | 0.20 | 79 | 94 | 0.77 | 68 |
| | 14 | MCO | 1.37 | 133 | 0.68 | 100 | 121 | 0.21 | 91 | 115 | 0.28 | 86 | 106 | 0.36 | 79 | 88 | 1.23 | 66 |
| | 15 | MCO | 2.70 | 130 | 0.22 | 100 | 121 | 0.37 | 93 | 113 | 0.40 | 87 | 103 | 0.38 | 79 | 83 | 0.15 | 63 |
| | 18 | OYAPE | 0.59 | 137 | 1.22 | 100 | 131 | 0.33 | 95 | 121 | 0.42 | 88 | 110 | 0.64 | 80 | 88 | 1.42 | 64 |
| | 19 | OYAPE | 1.18 | 135 | 0.78 | 100 | 127 | 0.34 | 94 | 121 | 0.25 | 89 | 111 | 0.68 | 82 | 90 | 1.60 | 66 |
| | 20 | OYAPE | 2.33 | 129 | 0.60 | 100 | 117 | 0.55 | 90 | 108 | 0.62 | 83 | 96 | 0.63 | 74 | 77 | 1.12 | 59 |
| | 21 | BBAPE | 0.69 | 131 | 0.63 | 100 | 120 | 0.28 | 91 | — | — | — | — | — | — | — | — | — |
| | 22 | BBAPE | 1.47 | 126 | 0.43 | 100 | 121 | 0.56 | 96 | 114 | 0.55 | 91 | 101 | 3.4 | 80 | 71 | 2.6 | 56 |

Figure 8:
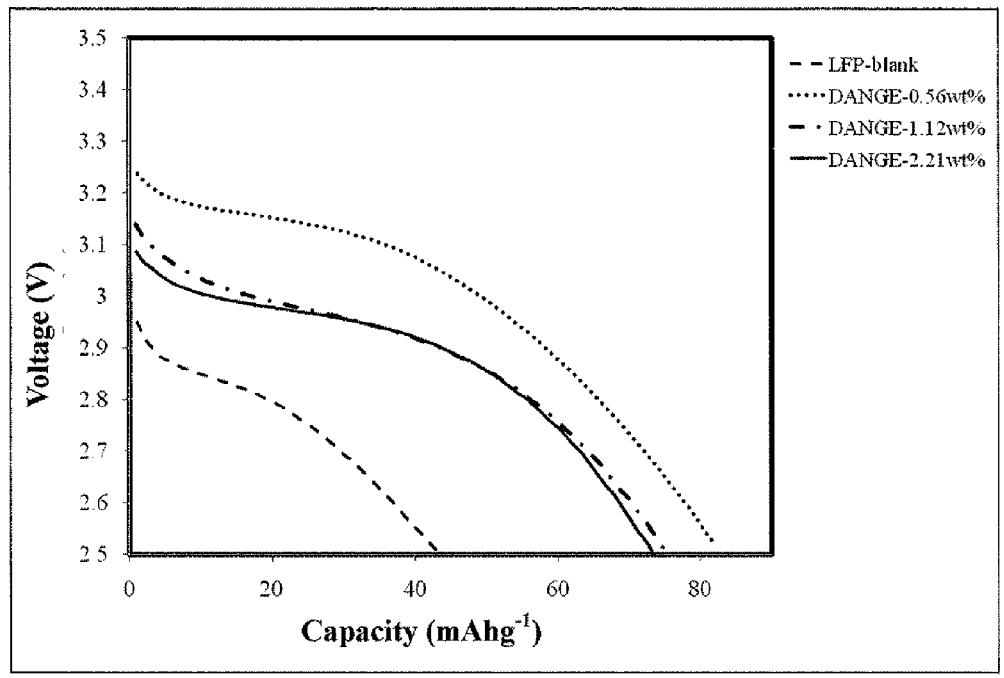
FIG. 8 is a charging/discharging curve showing the relation between the capacity at 1 C, 2 C, 3 C, or 5 C discharge rate and the voltage of the batteries according to the comparative example 1 and the example 1.

In addition, the discharge capacities at 5 C of the examples 1, 2 and 3 in the Table 5 were collected and plotted as charge/discharge curves for comparison as shown in FIG. 8. The symbols of the comparative example 1 and each of examples were listed in Table 6.

TABLE 6 conversion table of symbols

| Figure | Symbol | Corresponding example or comparative example |
|---|---|---|
| FIG. 8 | — — — — | Comparative example 1 |
|  | •••••••••• | Example 1 |
|  | — · — | Example 2 |
|  | ▬▬▬▬ | Example 3 |

[Result]:

From the test results of the above-mentioned examples as shown in Tables 2, 3, and 5, the batteries using the electrolytes formulated in accordance with the formulations of the present invention were superior to that using the electrolyte without additive in most properties, especially in the discharge capacity of first cycle (i.e. $1^{st}$ discharge capacity) and irreversibility percentage.

Please refer to the tested results of additives with regard to capacities obtained by charge/discharge at 1 C rate at different concentrations at 25° C., as shown in FIGS. 2, 4, and 6. The tested results indicated that the example 1 had unobvious effect while the examples 5 and 6 with enhanced concentration of additive had very good effect. Besides, on the contrary, the capacity according to the example 5 or 6 with enhanced concentration of additive was inferior to that according to the example 4. The effects of the examples 21 and 22 were both extremely good and the effects of the examples 13, 14, and 15 were next.

FIGS. 3, 5, and 7 showed the tested results at 60° C. The example 4 had a superior tested result to the examples 5 and 6 with higher concentration of additive that is the same as the tested result at 25° C. The example 1 also had a superior tested result to the examples 2 and 3 with higher concentration of additive. Among the examples 7, 8, and 9 with the same additive, the tested results of the examples 8 and 9 with enhanced concentration of additive were quite good. In addition, the effect of the example 12 was also quite good and the effect of the example 11 with lower concentration of additive was next. As for the whole of tested results at higher temperature, the examples except for the example 13 were able to perform their function that is enhancing the capacity or retarding the degradation of capacity.

FIG. 8 showed that the discharge capacities at 5 C rate of the examples 1, 2, and 3 were higher than the discharge capacity at 5 C rate of the comparative example 1 without additive by many amounts, wherein the effect of the example 1 with lowest concentration of additive was particularly outstanding.

Figure 9:
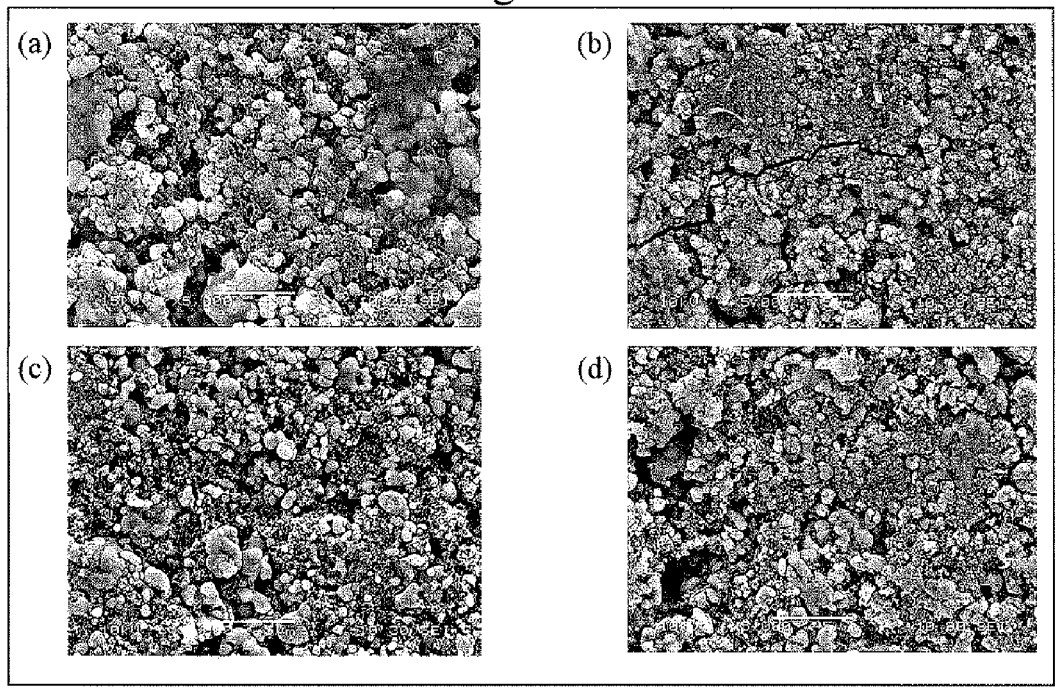
FIG. 9 is a SEM image (5000×) showing the surface of the electrode (lithium iron phosphate) according to the comparative example 1 and the examples 1, 2, and 3 after the batteries are charged and discharged for 100 times at room temperature (i.e. 25° C.), wherein (a), (b), (c), and (d) are the comparative example 1, the example 1, the example 2, and the example 3, respectively.
Figure 10:
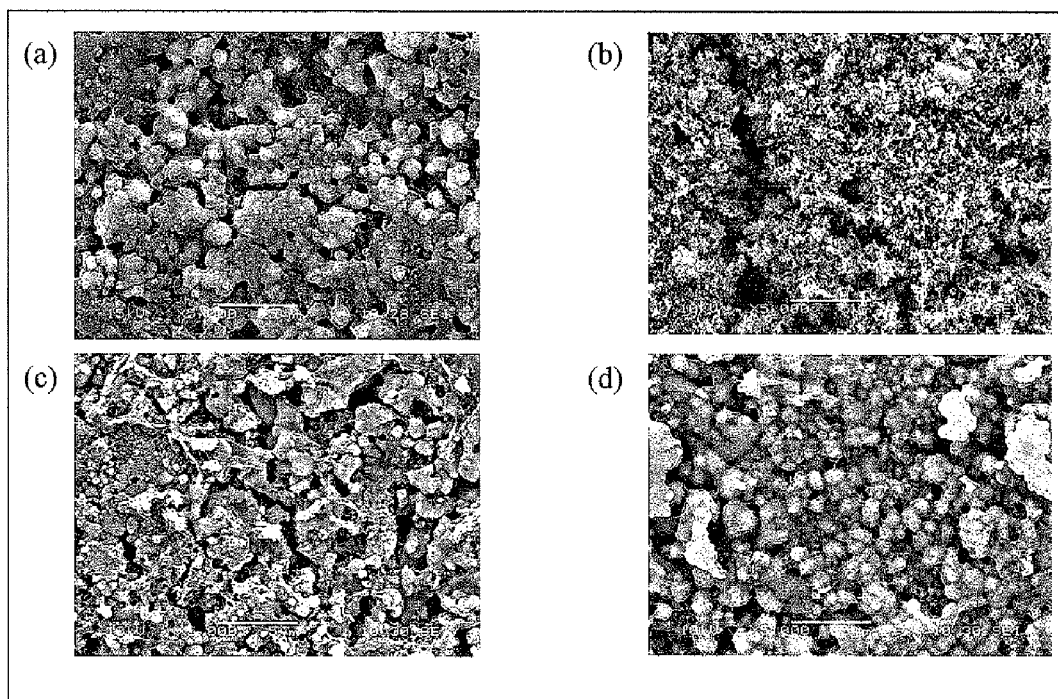
FIG. 10 is a SEM image (5000×) showing the surface of the electrode (lithium iron phosphate) according to the comparative example 1 and the examples 1, 2, and 3 after the batteries are charged and discharged for 100 times at 60° C., wherein (a), (b), (c), and (d) are the comparative example 1, the example 1, the example 2, and the example 3, respectively.

FIG. 9 and FIG. 10 exhibited the surface images of the electrode sheets according to the comparative example 1 and the examples 1, 2, and 3 at 1 C charge/discharge rate at room temperature and higher temperature (60° C.), respectively. On the surface of the electrode sheet according to the comparative example 1 without additive, passive films produced at room temperature and higher temperature (60° C.) were obviously observed, in which the thickness of the passive films produced at higher temperature was thicker. In the examples 1, 2, and 3 with additive, the passive films produced at room temperature were thinner and more even and the appearances of the passive films produced at three concentrations were quite similar. At higher temperature, the thickness of the passive films was enhanced with increase of the concentration of additive. Besides, it was notable that the surface of the electrode sheet in the example 1 was covered with a layer of whiskery substance. We guessed that the influence of this surface morphology on batteries was positive from capacities and cycle properties of Table 2.

In sum, in the present invention, the boron-based additive is added to an electrolyte (such as 1M $LiPF_6$ EC/DMC (1:1)) for an electrochemical device (such as lithium battery) and used with a selected positive electrode material (such as lithium iron phosphate) and then assembled to obtain a coin cell. The coin cell was further tested for cycle life at higher temperature (60° C.). From experimental results, the cycle property at higher temperature of lithium iron phosphate as a positive electrode material is improved indeed by adding the boron-based additive to an electrolyte. Besides, with respect to the choice of the concentration of the boron-based additive, the applicant discovers that it is most preferable that the boron-based additive is present in an amount of 0.2 wt % to 5.0 wt % in the electrolyte after repeated test.

Other Embodiments

All characteristics disclosed herein can be combined in any combination. And the characteristics disclosed herein can be replaced by any characteristics to be used for the same, equal, or similar purpose. Thus, unless otherwise specified, the characteristics disclosed herein are examples of a series of equal or similar characteristics.

In addition, based on the disclosure herein, appropriate changes and modifications may be made by those skilled in the art according to different uses and situations without departing from the spirit and scope of the invention. Therefore, other embodiments are included in the claims of the present invention.

What is claimed is:

1. An electrolyte for an electrochemical device, comprising:
9.95-19.95 wt % of a salt,
80.0-90.0 wt % of a non-aqueous solvent, and
0.05-10.00 wt % of an additive comprising a compound represented by following formula:

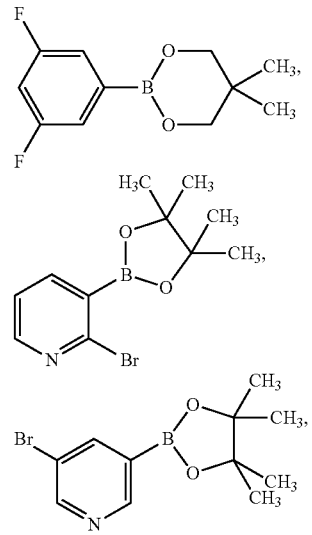

-continued

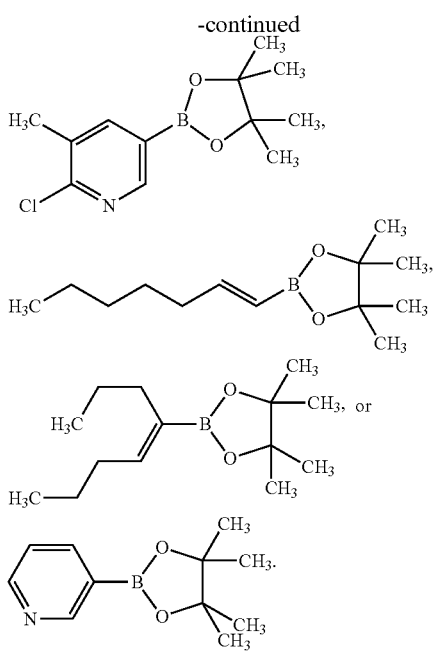

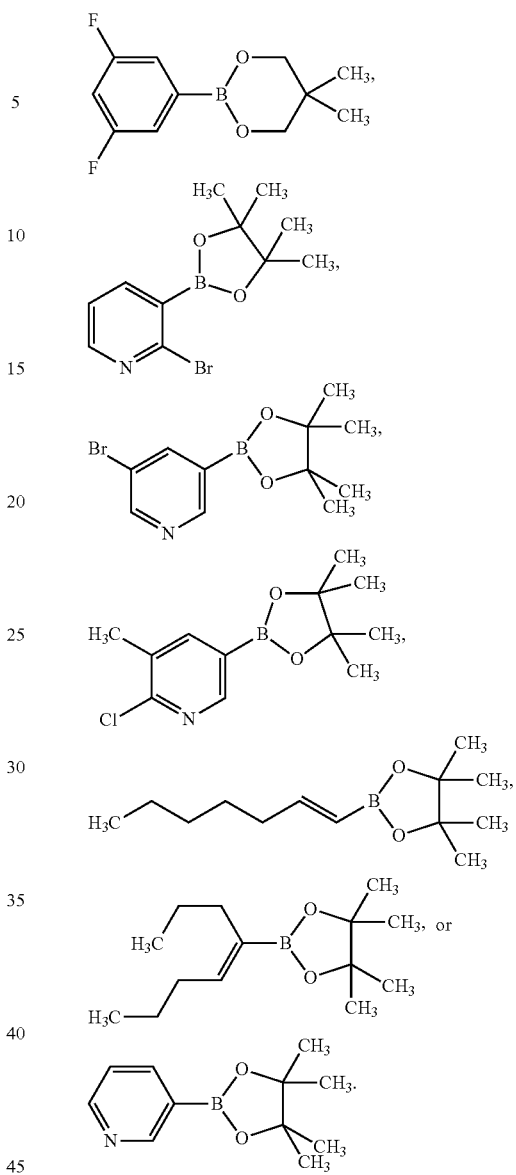

2. The electrolyte according to claim 1, wherein the salt is present in an amount of 11.0-12.0 wt %.

3. The electrolyte according to claim 1, wherein the additive is present in an amount of 0.2-5.0 wt %.

4. The electrolyte according to claim 1, wherein the salt is $LiPF_6$, $LiBF_4$, $LiN(CF_3SO_2)_2$, $LiCF_3SO_3$, or a mixture of the above.

5. The electrolyte according to claim 1, wherein the non-aqueous solvent is carbonates, furans, ethers, thioethers, nitriles, or a mixture of the above.

6. The electrolyte according to claim 1, wherein the non-aqueous solvent is ether polymers, polymethacrylate polymers, polyacrylate polymers, fluoropolymers, or combination thereof.

7. An electrochemical device, comprising a positive electrode, a negative electrode, and the electrolyte according to claim 1.

8. The electrochemical device according to claim 7, which is a lithium ion secondary battery.

9. A method for enhancing cycle property of electrochemical device, comprising adding an additive comprising a compound represented by following formula:

* * * * *